United States Patent [19]

Meilland, deceased

[11] Patent Number: Plant 6,892

[45] Date of Patent: Jul. 4, 1989

[54] ROSE PLANT—MEIVIOLIN VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 187,312

[22] Filed: Apr. 28, 1988

[51] Int. Cl.[4] ..... A01H 5/00

[52] U.S. Cl. ..... Plt./2

[58] Field of Search ..... Plt./2

*Primary Examiner*—James R. Feyrer

*Attorney, Agent, or Firm*—Burns, Doane, Swecker & Mathis

[57] ABSTRACT

A new and distinct variety of climbing shrub rose plant is provided which forms attractive very double creamy white blossoms which exhibit an ancient rose shape and are edged with carmine pink. The new variety exhibits vigorous vegetation and reflowers well during the summer. Excellent resistance to frost is present. The new variety is well adapted for growing as a landscape planting.

1 Drawing Sheet

SUMMARY OF THE INVENTION

The new variety of climbing shrub rose plant of the present invention was created by artificial pollination wherein two parents were crossed which previously had been studied in the hope that they would contribute the desired characteristics. The female parent (i.e., the seed parent) of the new variety was formed by crossing the Danse Des Sylphes variety (non-patented) by the Haender variety (non-patented). The male parent (i.e., the pollen parent) of the new variety was the Climbing Pink Wonder variety (non-patented). The parentage of the new variety can be summarized as follows:

[Danse Des Sylphes × Haender] × [Climbing Pink Wonder].

The seeds resulting from the above pollination were sown and 360 plantlets were obtained which were physically and biologically different from each other. Selective study resulted in the identification of a single plant of the new variety.

It was found that the new variety of climbing shrub rose plant of the present invention possesses the following combination of characteristics:

(a) abundantly and continuously forms attractive long lasting very double creamy white blossoms edged with carmine pink which exhibit an ancient rose shape,
(b) exhibits vigorous vegetation,
(c) exhibits excellent resistance to frost, and
(d) is particularly well suited for growing in the landscape.

The new variety well meets the needs of the horticultural industry. It can be grown to advantage as an attractive ornamentation in parks, gardens, public areas, and residential landscapes.

The characteristics of the new variety have been found to be homogeneous and stable and are strictly transmissible by asexual propagation from one generation to another.

The new variety has been named the Meiviolin variety.

BRIEF DESCRIPTION OF THE PHOTOGRAPH

The accompanying photograph shows, as nearly true as it is reasonably possible to make the same in a color illustration of this character, typical specimens of plant parts of the new variety. The rose plants of the new variety described herein were grown in the open air during June on *Rosa froebelii* at Cannet-des-Maures, Var, France.

DETAILED DESCRIPTION

Figures 1, 2, 3, 4, 5, 6, 7, 8, 9, 10, 11, 12, 13, 14, 15, 16:
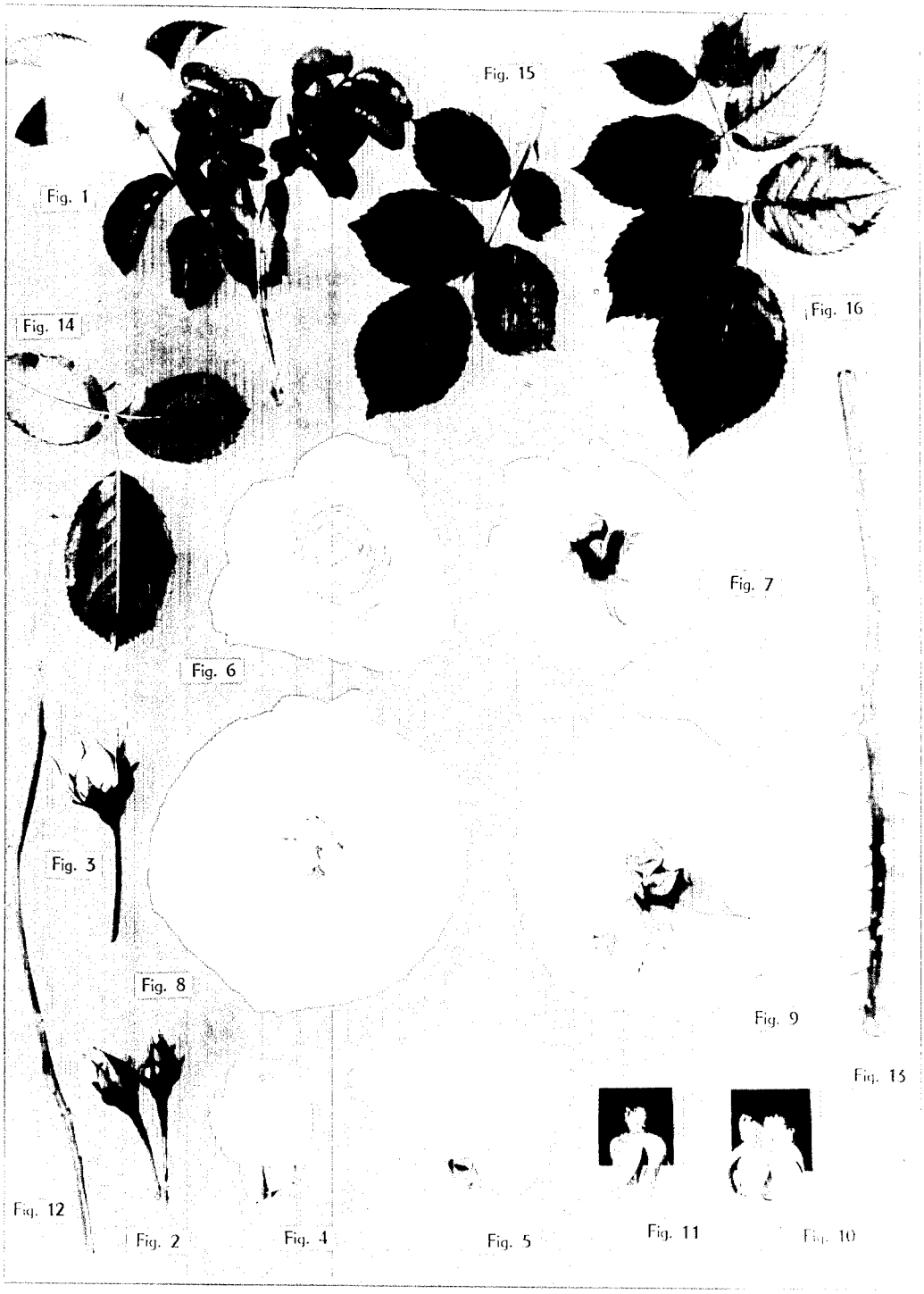
FIG. 1 illustrates a specimen of a young shoot.
FIG. 2 illustrates specimens of two floral buds before the opening of the sepals.
FIG. 3 illustrates a specimen of a floral bud at the opening of the sepals.
FIG. 4 illustrates a specimen of a floral bud as the petals open.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—under surface.
FIG. 15 illustrates a specimen of a leaf with five leaflets—upper surface.
FIG. 16 illustrates a specimen of a leaf with seven leaflets—upper surface.

The chart used in the identification of colors is that of The Royal Horticultural Society (R.H.S. Colour Chart). The description is based on two year old specimens of the new variety during June while grown in the open air on *Rosa froebelii* at Cannet-des-Maures, Var, France.

Class: Climbing Shrub.

Plant:

*Height.*—Approximately 80 to 140 cm. on average.

*Habit.*—Climbing.

Branches:

*Color.*—Young stems: light green, Yellow-Green Group 146D. Adult wood: light green, Yellow-Green Group 146C.

Leaves:

*Stipules.*—Adnate, pectinate, wide and linear.

*Petioles.*—Upper surface: grooved, reddish-brown on young foliage, medium green on mature foliage with more or less glandular edges. Under surface: light green with some small hooked thorns.

*Leaflets.*—Number: 3, 5, and 7 (most often). Shape: oval. Serration: simple and regular. Texture: firm. Overall appearance: dense foliage with a semi-glossy aspect. Color (young foliage): upper surface: lettuce green, Yellow-Green Group 144A, widely shaped with a reddish tint. under surface: lettuce green, Yellow-Green Group 144A, widely shaded with a reddish tint. Color (adult foliage): upper surface: light medium green, Yellow-Green Group 147A. under surface: light green, Yellow-Green Group 147B.

Inflorescence:

*Number of flowers.*—Generally one blossom per stem.

*Peduncle.*—Smooth, green, straight, rigid, quite long, approximately 7 cm. in length on average.

*Sepals.*—Upper surface: tomentose, greenish in coloration. Under surface: medium green in coloration with a reddish tint, often with glandular appendiculated edges.

*Buds.*—Shape: globular. Length: approximately 3.0 cm on average. Color: upper surface: greenish creamy white, White Group 155A, edged with a thin border of carmine pink, Red Group 52C. Under surface: substantially the same as the upper surface.

*Flower.*—Form: very double, as a hollow cup with a flat top. Diameter: approximately 8 to 10 cm. on average. Color (when opening begins): upper surface: creamy white, White Group 155A, edged with a thin border of carmine pink, Red Group 52C, and lightly suffused particularly on the center petals with pale carmine pink, Red Group 52D. under surface: substantially the same as the upper surface. Color (when partially open): upper surface: as above. under surface: as above. Color (at end of opening): upper surface: creamy white, White Group 155A, lightly diffused with pale carmine pink, Red Group 52D. under surface: substantially the same as the upper surface. Fragrance: light. Flower duration: long. Petal form: flattened with more or less reflected edges. Petal texture: firm. Petal number: approximately 55 to 60. Petal drop: good. Stamen number: approximately 120 to 125 on average. Anthers: normal, straw yellow in coloration and edged with dark ochre. Filaments: normal, yellowish. Pistils: approximately 80 to 90 on average. Stigmas: normal, straw colored, located beyond the anthers. Styles: free, straw colored with a bright violet top, of very irregular heights. Receptacle: medium green at dehiscence of the anthers, and in longitudinal section it is wide and in the shape of a jug.

Development:

*Vegetation.*—Vigorous.

*Blossoming.*—Abundant and continuous.

*Aptitude to bear fruits.*—None.

*Resistance to frost.*—Very good.

*Resistance to diseases.*—Good.

I claim:

1. A new and distinct variety of climbing shrub rose plant characterized by the following combination of characteristics:

(a) abundantly and continuously forms attractive long lasting very double creamy white blossoms edged with carmine pink which exhibit an ancient rose shape, (b) exhibits vigorous vegetation, (c) exhibits excellent resistance to frost, and (d) is particularly well suited for growing in the landscape, substantially as herein shown and described together with the parts thereof.

* * * * *